United States Patent [19]

Disch et al.

[11] Patent Number: 4,661,523

[45] Date of Patent: Apr. 28, 1987

[54] DISINFECTANT SOLUTIONS HAVING IMPROVED CORROSION PROPERTIES

[75] Inventors: Karlheinz Disch, Haan; Klaus Hachmann, Hilden; Juergen Pagel, Duesseldorf, all of Fed. Rep. of Germany

[73] Assignee: Henkel Kommanditgesellschaft auf Aktien, Duesseldorf, Fed. Rep. of Germany

[21] Appl. No.: 792,361

[22] Filed: Oct. 29, 1985

[30] Foreign Application Priority Data

Oct. 29, 1984 [DE] Fed. Rep. of Germany ....... 3439519

[51] Int. Cl.$^4$ .................... A01N 37/52; A01N 33/12; C11D 3/48
[52] U.S. Cl. .................................. 514/635; 252/106; 514/642; 514/643
[58] Field of Search ............... 514/362, 635, 642, 643; 252/106

[56] References Cited

U.S. PATENT DOCUMENTS

| | | | |
|---|---|---|---|
| 2,921,908 | 1/1960 | McCune | 252/110 |
| 3,932,655 | 1/1976 | Conn | 514/574 |
| 4,010,252 | 3/1977 | Hewitt | 424/47 |
| 4,206,233 | 6/1980 | Quinlan | 514/642 |
| 4,379,137 | 4/1983 | Ehlers et al. | 514/373 |
| 4,443,363 | 4/1984 | Klinger et al. | 252/547 |
| 4,443,364 | 4/1984 | Klinger et al. | 252/547 |

FOREIGN PATENT DOCUMENTS

| | | |
|---|---|---|
| 882803 | 8/1980 | Belgium . |
| 2415981 | 9/1975 | Fed. Rep. of Germany . |
| 2141982 | 10/1975 | Fed. Rep. of Germany . |
| 2637363 | 3/1977 | Fed. Rep. of Germany . |
| 2611957 | 9/1977 | Fed. Rep. of Germany . |
| 0766831 | 5/1976 | Japan . |

OTHER PUBLICATIONS

European Search Report EP 85 11 3325.
Roempps Chemie Lexikon, 7th Ed., p. 2644 (1974).
Chem. Abst. 99: 179934(b) (1983)–Show a Industries Co.
Chem. Abst. 98: 187,956e (1983)–Marshall.
Chem. Abst. 95: 185,759g (1981)–Letartre.
Chem. Abst. 94: 138139z (1981)–Laboratories Anios S.A.r.l.
Chem. Abst. 89: 129707c (1978)–Dingwall et al.
Chem. Abst. 88: 109373s (1978)–Abiko et al.
Chem. Abst. 83: 15460n (1975)–Kallfass et al.
Chem. Abst. 72: 113090j (1970)–Hellsten et al.

*Primary Examiner*—Douglas W. Robinson
*Attorney, Agent, or Firm*—Ernest G. Szoke; Henry E. Millson, Jr.; Mark A. Greenfield

[57] ABSTRACT

Phosphonocarboxylic acids, such as phosphonosuccinic acid and especially 2-phosphonobutane-1,2,4-tricarboxylic acid, and aminopolycarboxylic acids, advantageously tetrasodium trimethylene diamine tetracetate or trisodium nitrilotriacetate, are added to aqueous or aqueous solvent-containing disinfectant solutions based on aldehydes and quaternary ammonium compounds for corrosion inhibition and pH-adjustment to 3.5–4.0, respectively. The corrosion inhibiting effect of the two salts is synergistic.

15 Claims, No Drawings

DISINFECTANT SOLUTIONS HAVING IMPROVED CORROSION PROPERTIES

BACKGROUND OF THE INVENTION

1. Field of the Invention

The present invention relates to aqueous or aqueous solvent containing disinfectant solutions having improved corrosion properties.

2. Description of Related Art

Immediately after use, medical instruments are placed in an aqueous solution of disinfectants for cleaning and disinfection. The resulting destruction of vegetative germs and spores depends on the concentration and contact time of the disinfectant solution.

Commercially available disinfectant solutions contain as antimicrobial agents, inter alia, phenol derivatives, active chlorine donors, quaternary ammonium compounds or aldehydes or mixtures of these agents, preferably mixtures of quaternary ammonium compounds and aldehydes of the type known, for example, from German Application No. 26 11 957. While these agents are performing their disinfecting functions, however, the treated surfaces, especially the surfaces of instruments and appliances, have to be protected against corrosive attack. Accordingly, it is important to prevent corrosion by disinfectants without impairing the level of disinfection.

German Pat. No. 2,141,982 relates to disinfectants having a particularly strong cleaning and disinfecting effect comprising a combination of quaternary ammonium compounds and phosphonocarboxylic acids, such as 2-phosphonobutane-1,2,4-tricarboxylic acid and salts thereof, the latter acting as sequestrants. However, it is known, for example from Roempps Chemie-Lexikon, 7th Edition (1974), page 2644, that 2-phosphonobutane-1,2,4-tricarboxylic acid is also a basic ingredient of corrosion inhibitors.

This is also apparent from Japanese Patent Application No. 76/6831, according to which, inter alia, nitrilotriacetic acid and ethylene diamine tetracetic acid can also be added.

Accordingly, 2-phosphonobutane-1,2,4-tricarboxylic acid was added to known commercial disinfectants based on aldehydes and quaternary ammonium compounds in order thus to avoid any corrosive effects. However, it was found that this reduced the pH-value of disinfectant preparations to below pH 3.0, producing a serious deterioration in their stability. This could be prevented by adding sodium hydroxide and adjusting the pH-value to 3.5-4.0. However, even at higher pH-values, there was a deterioration in the stability of the prepared solutions.

Other sequestrants, such as salts of aminopolycarboxylic acids, also produced marked improvements in the corrosion behavior of disinfectants, provided the pH-value of the concentrate was reduced to pH 3.5-4.0 by addition of acids, for example formic acid, for reasons of stability.

DESCRIPTION OF THE INVENTION

Other than in the operating examples, or where otherwise indicated, all numbers expressing quantities of ingredients or reaction conditions used herein are to be understood as modified in all instances by the term "about."

It has now been found that the corrosion behavior of disinfectant concentrates and diluted solutions prepared therefrom which are based on aldehydes and quaternary ammonium compounds can be synergistically improved by adding to the concentrates from 0.2 to 5% by weight and preferably from 0.5 to 2.5% by weight, based on the concentrate as a whole, of at least one phosphonocarboxylic acid and adjusting the pH-value of the concentrate to pH 3.5-4.0 by addition of from 0.2 to 5% by weight and preferably from 0.4 to 4% by weight, based on the solution as a whole, of at least one aminopolycarboxylic acid salt.

Accordingly, the present invention relates to a process for improving the corrosion behavior of disinfectant solutions based on aldehydes and quaternary ammonium compounds by adding at least one phosphonocarboxylic acid to aqueous or aqueous-solvent-containing preparations of the active agents and then adjusting the pH-value of these concentrates to pH 3.5-4.0 by addition thereto of at least one salt of an aminopolycarboxylic acid.

The present invention also relates to aqueous or aqueous solvent-containing disinfectant concentrates and diluted solutions thereof which are based on aldehydes and quaternary ammonium compounds containing at least one phosphonocarboxylic acid and at least one salt of an aminopolycarboxylic acid, and having a pH-value of from 3.5 to 4.0.

In particular, the aqueous or aqueous solvent-containing disinfectant concentrates of the invention contain the following components, with percentages being by weight based on the concentrate as a whole:

A. from 5 to 50%, preferably from 10 to 30% of at least one aldehyde;
B. from 0.5 to 10%, preferably from 1.5 to 6% of at least one quaternary ammonium compound;
C. from 0.5 to 5.0%, preferably from 1.5 to 4.0%, and more preferably from 1.5 to 3.0% of a mixture of
   a. at least one phosphonocarboxylic acid or alkali metal salt thereof, and
   b. at least one aminopolycarboxylic acid salt, wherein the ratio by weight of a. to b. is in the range of from 1:0.5 to 1:0.9, and wherein b. is added in a quantity sufficient to provide a pH for the concentrate of from 3.5 to 4.0.

Component A. above is at least one aldehyde having bactericidal activity. Various mono- or dialdehydes containing from 1 to 5 carbon atoms, for example formaldehyde, acetaldehyde, propionaldehyde, glyoxal, isononyl aldehyde or glutardialdehyde, can be used as component A. in the disinfectant preparations of the invention. However, formaldehyde, glyoxal, glutardialdehyde, and mixtures thereof have proved to be particularly effective aldehydic components.

The quaternary ammonium compounds (component B) are the bactericidal compounds generally known and commonly used in the field of disinfectants, for example alkyl dimethyl benzyl ammoniumchloride, such as the compound known as benzalkonium chloride, benzyl dimethyl $C_{12}$–$C_{14}$ alkyl ammonium chloride, etc.; salts of oligomeric hexamethylene biguanide such as the water soluble mineral acid salts, e.g. oligohexamethylenebiguanide hydrochloride; dimethyl didecyl ammonium halides, e.g. the bromide or chloride; and the like.

The phosphonocarboxylic acid used as component C.a. is a phosphonosuccinic acid, such as phosphonosuccinic acid itself, or preferably 2-phosphonobutane-1,2,4-tricarboxylic acid or its alkali metal salt, e.g. its sodium or potassium salt.

Suitable aminopolycarboxylic acid salts for use as component C.b. are the tetra-alkali metal salts preferably the tetrasodium salt, of ethylenediamine tetracetic acid (EDTA) and, preferably, the trialkali metal salts, e.g. the trisodium salt, of nitrilotriacetic acid (NTA).

Since the disinfectants are processed and applied in the form of solutions, water and standard watermiscible organic solvents, particularly alcohols, such as ethanol or propanol, and glycols or ethers thereof, which are mixed with water, are used as solvents. The aqueous-solvent mixtures should contain at least 25% by weight of water.

Since the disinfectant solutions are required to perform a cleaning function in addition to their antimicrobial function, they can also contain nonionic surfactants as an optional ingredient. Suitable nonionic surfactants are adducts of from 4 to 40 moles and preferably of from 4 to 20 moles of ethylene oxide with 1 mole of fatty alcohol, alkyl cyclohexanol, alkyl phenol, fatty acid, fatty amine, fatty acid amide or alkane sulfonamide. Particularly suitable nonionic surfactants are the adducts of from 5 to 16 moles of ethylene oxide with coconut oil or tallow fatty alcohols, with oleyl alcohol and with mono-, dialkyl phenols or with monoalkylcyclohexanols containing from 6 to 14 C-atoms in the alkyl groups. The surfactants can be used in an amount of from 0.01 to 25% by weight and preferably of from 0.1 to 15% by weight, based on the weight of the concentrate.

In addition, the concentrates can optionally contain preparation aids, viscosity regulators, fragrances and/or dyes.

The concentrates of the invention can be used as such or can be diluted with water or a water-organic solvent mixture to as little as a 1% by volume solution of the concentrate in 99% by volume of water or water-organic solvent mixture, preferably from 1.5% to 10% solution of the concentrate therein. The water-organic solvent mixtures that can be employed are as disclosed above.

The concentrates or diluted solutions thereof of the invention can be used in all branches of human and veterinary medicine and, more specifically, in the home, in medical practice, in clinics, in hospitals and above all in surgery, in ear, nose and throat treatment, in dentistry, in urology, in gynaecology, and in obstetrics.

All medical appliances and instruments of metal, glass, plastics, rubber, etc. can be disinfected using the solutions of the invention, for example, respiratory apparatus of various types, anaesthetic equipment, breathing masks, incubators, breathing tubes, rubber gloves, endoscopic equipment, such as rectoscopes for example, other optical equipment, speculumns, etc. The instruments include, for example, scalpels, scissors, forceps, clamps, tweezers, needles, and syringes.

In addition to use of the solutions of the invention for disinfecting medical instruments, the solutions can of course also be used as disinfectants and preservatives in many other fields, for example in the surface, scrubbing or spraying disinfection of textiles, floors, hospital equipment, schools, swimming pools, public transport, industrial plants, industrial premises, and in stable disinfection.

In practice, the solutions of the invention are best applied at temperatures of from 10° to 40° C., and preferably at temperatures of from 15° to 30° C. At room temperature, bacteria are destroyed in 15 to 45 minutes, depending on the in-use concentration. In practice, however, the treatment time is extended to approximately one hour. However, if particularly rapid disinfection is required, more concentrated solutions can be applied and/or higher temperatures used in order to shorten the treatment time accordingly.

Another significant advantage of the preparations of the invention is their high stability in storage both in dilute ready-to-use form as well as in the form of their concentrates. The combined ingredients, namely aldehydes, quaternary ammonium compounds, phosphonocarboxylic acids and salts of aminopolycarboxylic acids, do not show any signs of incompatibility, even with prolonged storage.

The following Examples are intended to illustrate the invention without limiting it in any way.

EXAMPLES

Concentrates containing the compositions of the invention, from which ready-to-use disinfectants are obtained by dilution with water or aqueous solvents, were prepared having the following compositions (EO stands for ethylene oxide and all percentages given are based on the active substance content of the starting materials):

| | | |
|---|---|---|
| (A) | formaldehyde (35–40% aqueous solution) | 10 g |
| | dimethyl didecyl ammonium chloride | 3 g |
| | 2-phosphonobutane-1,2,4-tricarboxylic acid | 1.0 g |
| | $Na_4$—ethylene diamine tetracetate | 0.65 g |
| | dipropylene glycol methyl ether | 2.0 g |
| | isopropanol | 4.0 g |
| | water, fragrances to | 100 g |
| | pH (undiluted) | 3.6 |
| (B) | formaldehyde (35–40% aqueous solution) | 10 g |
| | glutardialdehyde (50% aqueous solution) | 10 g |
| | benzyldimethyl $C_{12}$–$C_{14}$—alkyl ammonium chloride | 2 g |
| | 2-phosphonobutane-1,2,4-tricarboxylic acid | 1.2 g |
| | $Na_3$—nitrilotriacetate | 0.7 g |
| | nonyl phenol.10 EO-adduct | 8 g |
| | 60% aqueous isopropanol solution to | 100 g |
| | pH (undiluted) | 3.5 |
| (C) | glutardialdehyde (50% aqueous solution) | 10 g |
| | benzyldimethyl $C_{12}$–$C_{14}$—alkyl ammonium chloride | 6 g |
| | 2-phosphonobutane-1,2,4-tricarboxylic acid | 0.8 g |
| | $Na_3$—nitrilotriacetate | 0.7 g |
| | $C_{12}$–$C_{18}$ fatty alcohol.7 EO-adduct | 8 g |
| | water, fragrances, dyes to | 100 g |
| | pH (undiluted) | 3.7 |
| (D) | formaldehyde (35–40% aqueous solution) | 10 g |
| | glyoxal (40% aqueous solution) | 12 g |
| | glutardialdehyde (50% aqueous solution) | 4 g |
| | benzyldimethyl $C_{12}$–$C_{14}$—alkyl ammonium chloride | 3 g |
| | phosphonocarboxylic acid: aminopoly-carboxylic acid salt = 1:0.5–0.9 | 0.5–5.0 g |
| | nonyl phenol.10 EO-adduct | 10 g |
| | ethanol | 6 g |
| | water, fragrance to | 100 g |
| | pH (undiluted) | 3.5–4.0 |
| (E) | glyoxal (40% aqueous solution) | 11 g |
| | isononyl aldehyde | 12 g |
| | dimethyl didecyl ammonium chloride | 4 g |
| | 2-phosphonobutane-1,2,4-tricarboxylic acid | 1.9 g |
| | $Na_3$—nitrilotriacetate | 1.5 g |
| | nonyl phenol.10 EO-adduct | 20 g |
| | ethanol:isopropanol = 1:1 | 10 g |
| | ·water to | 100 g |
| | pH (undiluted) | 3.6 |

Testing of corrosion behavior

An Article by H. Luedde published in "Die Pharmazie" 38, (1983), pages 892–893 describes a simple, highly sensitive corrosion test which reveals signs of corrosion, in some cases after only a few hours, through discoloration and rusting of standard commercially available nails. This nail corrosion test was used for studying the corrosion behavior of the disinfectant solutions prepared in accordance with the invention.

The prototype concentrate used (1.5% in water solution) was Example D) with varying amounts of 2-phosphonobutane tricarboxylic acid and salts of aminopolycarboxylic acids. The results are shown in the following Tables.

It can be seen from Table 1 that the use of 2% of known complexing agents in the concentrate produces a distinct improvement in corrosion behavior. Depending on the complexing agent, formic acid or NaOH was used for adjusting the pH of the concentrate to the range of 3.5–4.0 selected for all the tests for reasons of stability.

Table 2 shows the effect of inhibitor combinations made up of acidic and alkaline complexing agents in such a way that the target pH-range of 3.5–4.0 in the concentrate is reached without any additional pH correction.

The range of possible combinations of PBS and NTA was systematically investigated. The results are set out in Table 3. They show that corrosion behavior depends on the total concentration of the inhibitors and that, above 1.0% PBS, very good corrosion behavior can be achieved in pH-adjusted combinations with NTA. This corrosion behavior of the PBS and NTA combinations is better than the total concentration for a single inhibitor, proving that genuine synergism exists.

TABLE 1

Nail corrosion test with formulation D) of the Examples using various corrosion inhibitors (in-use concentration: 1.5%)
Appearance of the solutions: initial state = colorless, clear/after standing = unchanged

| Corrosion inhibitors | First signs[2] | Corrosion on nails after 24 h | 48 h | 72 |
|---|---|---|---|---|
| None | 4 h | — — — | — — — | — — — |
| 2% NTA[1] = trisodium salt of aminotricarboxylic acid | 50 h | 0 | 0 | — |
| 2% EDTA[1] = tetrasodium salt of ethylene diamine tetracetic acid | 50 h | 0 | 0 | — — |
| 2% PBS[1] = 2-phosphonobutane-1,2,4-tricarboxylic acid | none | 0 | 0 | 0 |

[1] = pH-adjustment with formic acid or NaOH to pH 3.5–4.0
[2] = nails black-gray in color
— — — = serious corrosion
— — = average corrosion
— = slight corrosion
0 = no corrosion

TABLE 2

Nail corrosion test with formulation D) of the Examples using inhibitor combinations (in-use concentration: 1.5%)

| Corrosion inhibitor combinations[1] | Appearance of the solutions after standing | First signs[2] | Corrosion on nails after 24 h | 48 h | 72 h |
|---|---|---|---|---|---|
| 2.2% PBS + 2% EDTA | colorless, clear | none | 0 | 0 | 0 |
| 2.2% PBS + 2% NTA | colorless, clear | none | 0 | 0 | 0 |
| 2% PBS + 1.3% EDTA | colorless, clear | none | 0 | 0 | 0 |
| 1.5% PBS + 1.1% NTA | colorless, clear | none | 0 | 0 | 0 |
| 1.0% PBS + 0.7% NTA | colorless, clear | 55 h | 0 | 0 | — |

[1] = pH settles at 3.5–4.0 in the concentrate
[2] = nails black-gray in color
— = slight corrosion
0 = no corrosion

TABLE 3

Nail corrosion test with formulation D) of the Examples using inhibitor combinations (in-use concentration: 1.5%)

| Total inhibitor concentration | Corrosion inhibitor combination | pH-value concentrate 3.5–4.0 | First signs[x] | Corrosion on nails after 24 h | 48 h | 72 h |
|---|---|---|---|---|---|---|
| 0.9% | 0.9% NTA | adjusted with HCOOH | 12 h | — | — — | — — — |
| | 0.9% PBS | adjusted with NaOH | 16 h | — | — — | — — — |
| | 0.5% PBS + 0.4% NTA | | 14 h | — | — — | — — — |
| 1.7% | 1.7% NTA | adjusted with HCOOH | 35 h | 0 | — | — — |
| | 1.7% PBS | adjusted with NaOH | 42 h | 0 | — | — — |
| | 1.0% PBS + 0.7% NTA | | 55 h | 0 | 0 | — |
| 2.6% | 2.6% NTA | adjusted with HCOOH | 45 h | 0 | (—) | (—) |
| | 2.6% PBS | adjusted with NaOH | 80 h | 0 | 0 | 0 |
| | 1.5% PBS + 1.1% NTA | | 90 h | 0 | 0 | 0 |
| 3.5% | 3.5% NTA | adjusted with HCOOH | — | 0 | (—) | (—) |
| | 3.5% PBS | adjusted with NaOH | — | 0 | 0 | 0 |
| | 2.0% PBS + 1.6% NTA | | — | 0 | 0 | 0 |
| 3.8% | 3.8% NTA | adjusted with HCOOH | — | 0 | (—) | (—) |
| | 3.8% PBS | adjusted with NaOH | — | 0 | 0 | 0 |

TABLE 3-continued

Nail corrosion test with formulation D) of the Examples using inhibitor combinations
(in-use concentration: 1.5%)

| Total inhibitor concentration | Corrosion inhibitor combination | pH-value concentrate 3.5-4.0 | Corrosion on nails | | | |
|---|---|---|---|---|---|---|
| | | | First signs[x] | after 24 h | 48 h | 72 h |
| | 2.2% PBS + 1.6% NTA | | — | 0 | 0 | 0 |

[x] = nails black-gray in color
0 = no corrosion
(—) = very slight corrosion
— = slight corrosion
— — = average corrosion
— — — = serious corrosion

What is claimed is:

1. A concentrated aqueous or aqueous organic solvent disinfectant composition comprising
 A. from about 5 to about 50% of at least one bactericidal aldehyde;
 B. from about 0.5 to about 10% of at least one bactericidal quaternary ammonium compound;
 C. from about 0.5 to about 5.0% of a mixture of
  a. at least one phosphonocarboxylic acid, and,
  b. at least one aminopolycarboxylic acid alkali metal salt, wherein the ratio by weight of a. to b. is in the range of from about 1:0.5 to about 1:0.9, wherein b. is added in a quantity sufficient to provide a pH for the concentrate of from about 3.5 to about 4.0, and
wherein the above percentages are percentages by weight based on the total weight of the composition.

2. A composition in accordance with claim 1 wherein component A. is present in from about 10 to about 30%.

3. A composition in accordance with claim 1 wherein component B. is present in from about 1.5 to about 6%.

4. A composition in accordance with claim 1 wherein component C. is present in from about 1.5 to about 4.0%.

5. A composition in accordance with claim 1 wherein component C. is present in from about 1.5 to about 3.0%.

6. A composition in accordance with claim 1 wherein component A. is a monoaldehyde or dialdehyde containing from 1 to 5 carbon atoms.

7. A composition in accordance with claim 1 wherein the phosphonocarboxylic acid is a phosphonosuccinic acid.

8. A composition in accordance with claim 7 wherein the phosphonocarboxylic acid is 2-phosphonobutane-1,2,4-tricarboxylic acid.

9. A composition in accordance with claim 1 wherein the aminopolycarboxylic acid alkali metal salt is the tetra-alkali metal salt of ethylenediamine tetraacetic acid, or the trialkali metal salt of nitrilotriacetic acid.

10. A composition in accordance with claim 1 wherein the composition also contains from about 0.01 to about 25% by weight of a nonionic surfactant.

11. A disinfectant solution wherein the concentrated composition of claim 1, 2, 3, 4, 5, 6, 7, 8, 9, or 10 is diluted with water or a water-organic solvent mixture.

12. A method of disinfecting a solid surface comprising contacting said surface with the composition of claim 1 as a concentrate or in diluted form.

13. A process for improving the corrosion resistance of a concentrated aqueous or aqueous-organic solvent disinfectant composition containing at least one bactericidal aldehyde and at least one bactericidal quaternary ammonium compound comprising adding thereto from about 0.5 to about 5.0% of a mixture of
 a. at least one phosphonocarboxylic acid, and
 b. at least one aminopolycarboxylic acid alkali metal salt wherein the ratio by weight of a. to b. is in the range of from about 1:0.5 to about 1:0.9, and wherein b. is added in a quantity sufficient to provide a pH for the concentrate of from about 3.5 to about 4.0, and
wherein the above percentages are percentages by weight based on the total weight of the composition.

14. A process in accordance with claim 13 wherein from about 1.5 to about 4.0% of said mixture is added to the composition.

15. A process in accordance with claim 14 wherein from about 1.5 to about 3.0% of said mixture is added to the composition.

* * * * *